(12) United States Patent
Barrows et al.

(10) Patent No.: US 8,481,677 B2
(45) Date of Patent: Jul. 9, 2013

(54) PROTEIN CONCENTRATE FROM STARCH CONTAINING GRAINS: COMPOSITION, METHOD OF MAKING, AND USES THEREOF

(76) Inventors: Frederic T Barrows, Bozeman, MT (US); Clifford A. Bradley, Missoula, MT (US); Robert D Kearns, Melrose, MT (US); Brian D Wasicek, Butte, MT (US); Ronald W Hardy, Twin Falls, ID (US)

( * ) Notice: Subject to any disclaimer, the term of this patent is extended or adjusted under 35 U.S.C. 154(b) by 753 days.

(21) Appl. No.: 12/424,145

(22) Filed: Apr. 15, 2009

(65) Prior Publication Data

US 2009/0259018 A1    Oct. 15, 2009

Related U.S. Application Data

(60) Provisional application No. 61/045,277, filed on Apr. 15, 2008.

(51) Int. Cl.
*C12P 21/00* (2006.01)
*C07K 2/00* (2006.01)

(52) U.S. Cl.
USPC .................. 530/300; 530/350; 435/68.1

(58) Field of Classification Search
USPC .................. 530/300, 350; 435/68.1
See application file for complete search history.

(56) References Cited

U.S. PATENT DOCUMENTS

| 4,624,805 A * | 11/1986 | Lawhon ............... 530/376 |
| 6,040,502 A * | 3/2000 | Threlkeld et al. ...... 800/312 |
| 7,968,318 B2 * | 6/2011 | Lantero et al. ........... 435/99 |

* cited by examiner

*Primary Examiner* — Chih-Min Kam
(74) *Attorney, Agent, or Firm* — Elizabeth R. Sampson; John D. Fado; Lesley Shaw

(57) ABSTRACT

The present invention relates to methods of producing a protein concentrate from a starch containing grain and uses thereof. In an exemplary embodiment, the protein concentrate produced is used to prepare an aquaculture feed.

10 Claims, 3 Drawing Sheets

PROTEIN CONCENTRATE FROM STARCH CONTAINING GRAINS: COMPOSITION, METHOD OF MAKING, AND USES THEREOF

RELATED APPLICATIONS

This application is claims priority to U.S. Provisional Patent Application Ser. No. 61/645,277, filed Apr. 15, 2008 the contents of which are incorporated herein by reference in their entirety.

FIELD OF THE INVENTION

Embodiments of the invention relate to processes for producing a protein concentrate from a starch containing grain or oil seed and uses thereof. In an exemplary embodiment, the protein concentrate produced using the disclosed processes comprises a high quality, highly digestible protein that is suitable for use as an aquaculture feed.

BACKGROUND OF THE INVENTION

Protein is an essential component of the diet of all domestic animals and is necessary for growth, body maintenance, the production of young and the output of meat and non-meat products e.g., milk, eggs and wool. Thus, for productive animal agriculture, protein is essential.

The protein, and hence amino acid requirements for most agriculturally important animals are well known in the art (see e.g., *The Encyclopedia of Farm Animal Nutrition*, M. F. Fuller (ed) 2004, Cabi Publishing). As is known in the art, requirements vary depending on the species and age of animals. For example, pastures and forage can play a major role in supplying ruminants with their protein needs, because the biota of ruminant animals synthesize amino acids and proteins de novo. But for some species e.g., fish, the provision of adequate nutrition, especially adequate protein, must come directly from the diet.

The raising of fish in aquaculture presents nutritional issues that are unique amongst agricultural animals. In particular, the protein allowances in fish diets are appreciably higher than those in the diets of terrestrial warm-blooded animals. Thus, aquaculture feeds characteristically contain a higher percent of protein than feeds used in agriculture to feed e.g., poultry, swine, and beef. However, it is not just the amount of protein that makes aquaculture feeds unique, but also the requirement for high quality protein (see e.g., J. W. Hertrampf, et al. (2000)*Handbook on Ingredients for Aquaculture Feeds*, Kluwer Academic Publishers; and Nutrient Requirements of Fish, Committee on Animal Nutrition, Board on Agriculture, National Research Council National Academy Press (1993)).

Aquaculture is the fastest growing food production sector in the world. Thus, addressing the needs of aquaculture practices promises to improve food and nutrition for the future of humanity. The biggest need in aquaculture is to provide feeds which supply sufficient high quality protein in a palatable form.

Aquaculture feeds typically comprise fishmeal as a source of protein. Unfortunately however, in recent years, the cost of fishmeal has increased, concerns have been raised about the residues of toxic pollutants e.g., dioxin, in fishmeal, regulation of nutrients in hatchery effluents has intensified, and questions regarding the sustainability of fishmeal as an aqua-feed ingredient have arisen. Thus, there is increased interest in finding alternatives to fishmeal that could be used either alone or in combination with fishmeal to provide nutritious aquaculture diets (see e.g., Hites, R. A. et al. (2004) Science 303: 226-229; Naylor, R. L. et. al. (2000). Nature 405: 1017-1024).

There are many possible sources of protein for aquaculture rations. Dietary protein can be derived from either or both plant and animal sources, but the choice of protein source must be carefully selected in order to provide high quality protein in a correct amount and with the appropriate balance of essential amino acids. The protein must be digestible and thus, bioavailable to the fish, and finally, since fish can be picky eaters, protein sources must also be palatable.

There are many possible sources of plant protein for livestock rations and naturally, grains and plant derived proteins have been considered as an alternative to fishmeal in aquaculture diets. Unfortunately however, protein concentration of plant sources are typically lower than fish meal, essential amino acids are lacking, protein digestibility may be poor and palatability of feeds prepared with plant derived proteins may be unpalatable to fish. Because of their relatively high protein concentration relative to other plant sources, soybeans and soybean meal have been extensively evaluated and are now used in aquaculture feeds particularly for non carnivorous species of farmed fish. (see e.g., Hardy, R. W. (2003) *Use of soybean meals in diets of salmon and trout*. Technical review paper, Managed Aquaculture Program, United Soybean Board, American Soybean Association. available through: American Soybean Association Headquarters, 12125 Woodcrest Executive Drive, Suite 100 St. Louis, Mo. 63141-5009) However, soy contains anti-nutritional compounds e.g., phytate, and/or undigestable carbohydrates e.g., oligosaccharides, and these anti-nutritional compounds limit the use of soy derived proteins in aquaculture feeds. This is a particular issue with feeds for species such as trout and salmon (see e.g., Knudsen, D., et al. (2007) Journal of Agriculture and Food Chemistry 55: 2261-2267; Knudsen, D., et al. (2006). Journal of Agriculture and Food Chemistry 54:6428-6435.

Thus, there exists a need in the art for plant based sources of high quality protein that is suitable for use in inter alia, aquaculture feeds. Fortunately, as will be clear from the following disclosure, the present invention provides for this and other needs.

SUMMARY OF THE INVENTION

In one embodiment, the invention provides a process for producing a protein concentrate from a starch containing grain or oil seed, wherein the method comprises: dehulling the grain or using a hulless variety, grinding the starch containing grain to produce a ground starch containing grain; slurrying the ground starch containing grain with water; solublizing starch and glucans with enzymes; adding a fermentation organism to the slurry; fermenting the slurry comprising the fermentation organism until fermentation is complete, thereby producing a fermented slurry; separating the fermented slurry into solid and liquid fractions; recovering the solid and liquid fractions; drying the recovered solid fraction at a temperature below that which would denature or damage proteins; thereby producing a protein concentrate.

In one exemplary embodiment, solublizing the starch and glucans with enzymes produces glucose.

In one exemplary embodiment, the process is a no-cook process wherein raw ungelatinized granular starch is hydrolyzed to glucose. In another exemplary embodiment, the process is a cooking process wherein a ground starch slurry is heated to a temperature which gelatinizes the starch granules.

In one exemplary embodiment, the process further comprises: distilling the recovered liquid fraction to recover a fermentation product. In another exemplary embodiment, the fermentation product is ethanol. In another exemplary embodiment, the starch containing grain is a member selected from the group consisting of barley, wheat, oats, corn, rye, tritcale, and sorghum, or a combination thereof. In another exemplary embodiment the starch containing grain is a starch containing oil seed e.g., soybeans, flax, camelina. Thus, in another exemplary embodiment, the starch containing grain is a processed grain e.g., an oilseed meal e.g., soybean meal. In one exemplary embodiment, the starch containing grain is barley. In another exemplary embodiment, the barley is hulless. In another exemplary embodiment, the barley is mechanically de-hulled.

In another exemplary embodiment, the invention provides a protein concentrate made according to a process for producing a protein concentrate from a starch containing grain, wherein the process comprises: grinding the starch containing grain to produce a ground starch containing grain; slurrying the ground starch containing grain with water; solublizing starch and glucans with enzymes; adding a fermentation organism to the slurry; fermenting the slurry comprising the fermentation organism until fermentation is complete, thereby producing a fermented slurry; separating the fermented slurry into solid and liquid fractions; recovering the solid and liquid fractions; drying the recovered solid fraction at a temperature below that which would denature or damage proteins; thereby producing a protein concentrate. In one exemplary embodiment, the protein concentrate comprises protein in an amount that is in a range that is between about 30% protein to about 65% protein on a dry basis.

In another exemplary embodiment, the invention provides an aquaculture feed comprising a plant protein made according to a process for producing a protein concentrate from a starch containing grain, wherein the process comprises: grinding the starch containing grain to produce a ground starch containing grain; slurrying the ground starch containing grain with water; solublizing starch and glucans with enzymes; adding a fermentation organism to the slurry; fermenting the slurry comprising the fermentation organism until fermentation is complete, thereby producing a fermented slurry; separating the fermented slurry into solid and liquid fractions; recovering the solid and liquid fractions; drying the recovered solid fraction at a temperature below that which would denature or damage proteins; thereby producing a protein concentrate.

In another exemplary embodiment, the invention provides a process for producing a protein concentrate with an increased protein concentration from a starch containing grain or oil seed, wherein the method comprises: dehulling the grain or using a hulless variety, grinding the starch containing grain to produce a ground starch containing grain; slurrying the ground starch containing grain with water; solublizing starch and glucans with enzymes; adding a fermentation organism to the slurry; fermenting the slurry comprising the fermentation organism until fermentation is complete, thereby producing a fermented slurry; separating the fermented slurry into solid and liquid fractions; recovering the solid and liquid fractions; culturing an appropriate microbe to provide a cell mass in a culture medium comprising the recovered liquid fraction recovered, recovering the cell mass with the grain solids, and drying the recovered solid fraction at a temperature below that which would denature or damage proteins; thereby producing a protein concentrate.

In one exemplary embodiment the appropriate microbes is a member selected from the group consisting of *Rhizopus oryzae* and *Rhizopus microsporus*.

In another exemplary embodiment, the invention provides a method for producing a protein concentrate with an increased protein concentration from a starch containing grain, the method comprising: grinding the starch containing grain to produce a ground starch containing grain; slurrying the ground starch containing grain with water; solublizing starch and glucans with enzymes; adding an appropriate organism selected for cell mass production to the slurry; fermenting the slurry comprising the organism until fermentation is complete, thereby producing a slurry in which soluble sugars have been converted to cell mass; separating the slurry into solid and liquid fractions; recovering the solid and liquid fractions; recovering the cell mass with the grain solids, and drying the recovered solid fraction at a temperature below that which would denature or damage proteins; thereby producing a protein concentrate with an increased protein concentration. In one exemplary embodiment, the appropriate microbe is a member selected from the group consisting of *Rhizopus oryzae* and *Rhizopus microsporus*. In another exemplary embodiment, the invention provides a protein concentrate made by the method. In still another exemplary embodiment, the protein concentrate made by the method is a soy protein concentrate with reduced or eliminated phytate and reduced or eliminated anti-nutritional factors.

Other features, objects and advantages of the invention will be apparent from the detailed description which follows.

DETAILED DESCRIPTION OF THE INVENTION

Definitions

Figure 1:
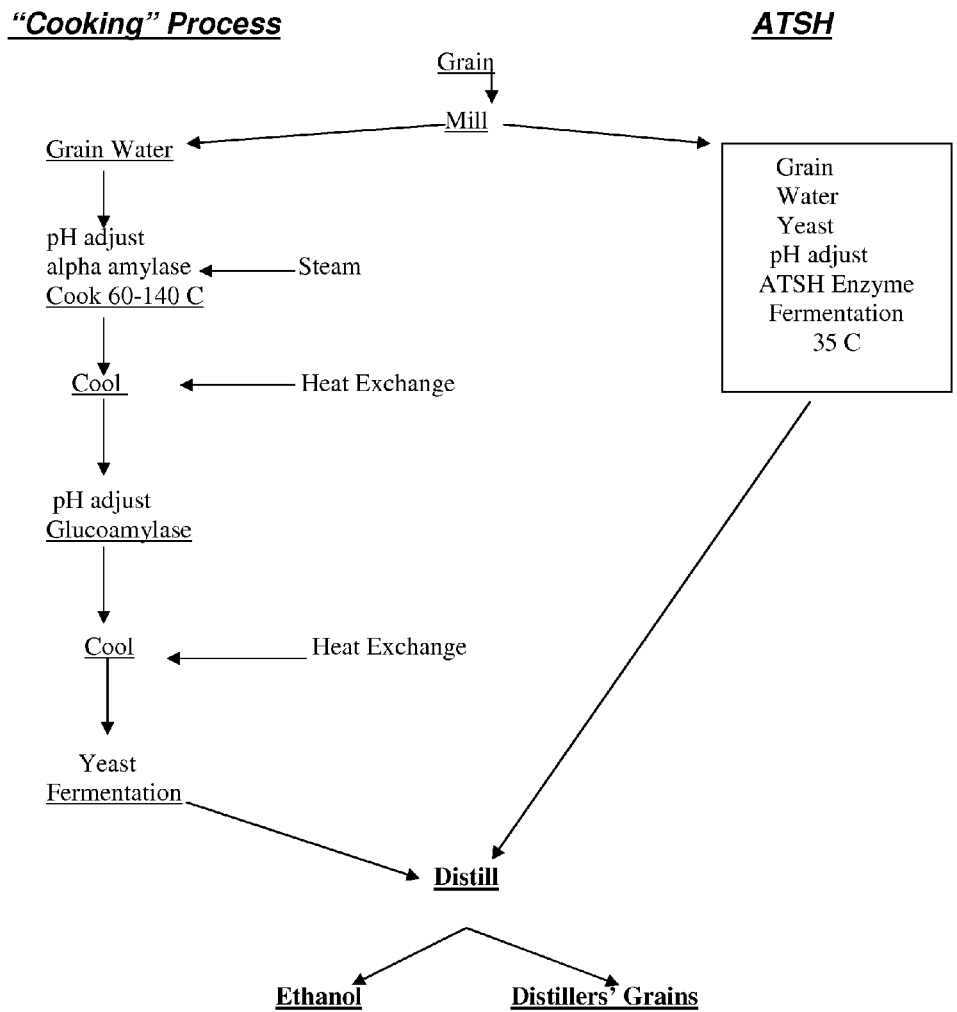
FIG. 1. Is a flow diagram illustrating on the left side, ethanol production using standard commercial dry mill processes. The left side of the flow diagram illustrates the conventional cooking process used in converting starch to fermentable sugars. The right side illustrates the process for conventional a "no cook" process.
Figure 2:
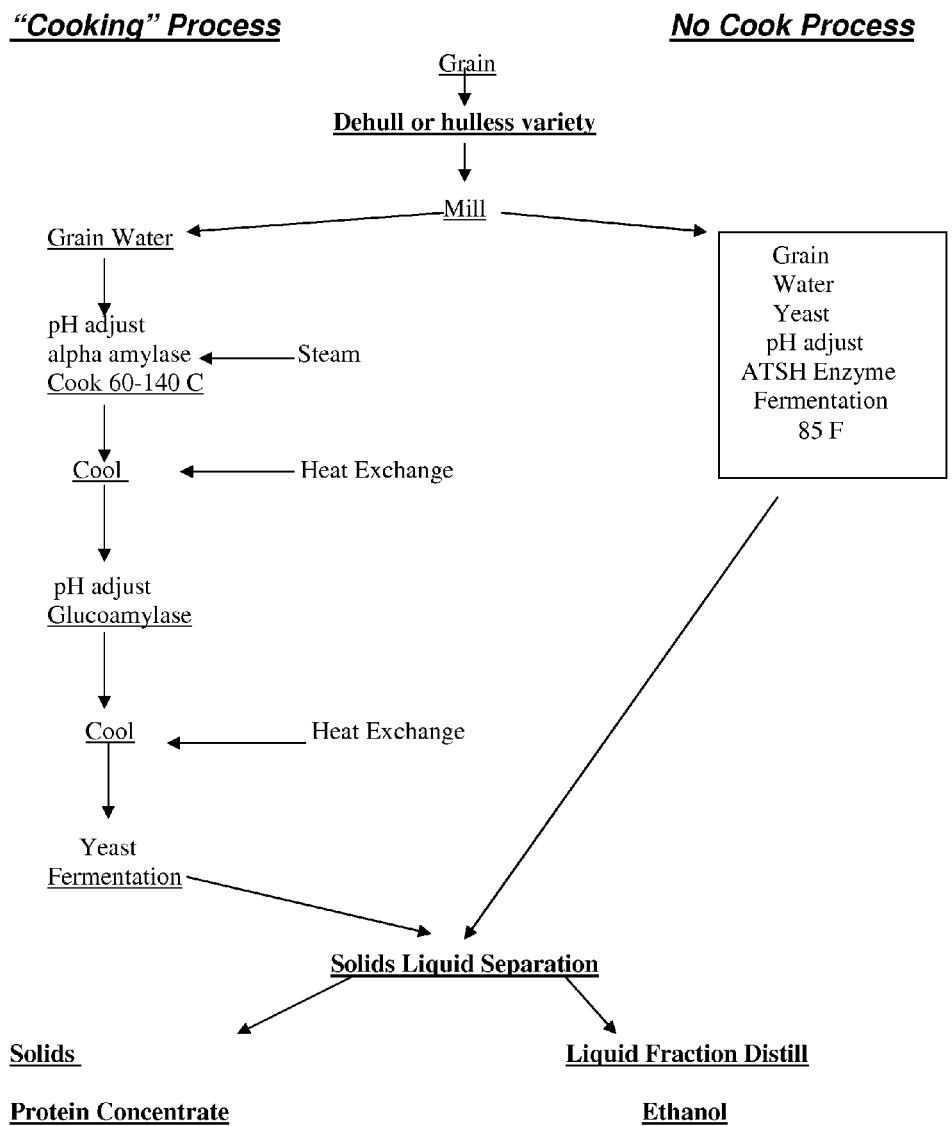
FIG. 2 Is a flow diagram illustrating on the left side, the production of a protein concentrate and ethanol production using the disclosed processes. The left side of the flow diagram illustrates the cooking process. The right side illustrates the process for conventional a "no cook" process.

The term "protein concentrate" as used herein refers to proteins that are isolated from their native source, e.g., proteins isolated from a starch containing grain or oil seed. Typically, the isolated proteins are in a more concentrated form than they are in their native state.

The term "starch containing grain" as used herein refers to grains that provide sources of carbohydrate, typically in the form of starch. Exemplary starch containing grains include, but are not limited to cereal grains and seeds or "pseudocereals". The term "cereal grain" is used conventionally herein and refers generally to the edible grain of the members of the grass family. Exemplary cereal grains from grass family plants include but are not limited to e.g., oats, barley, wheat, corn, flax, hops, rice, rye, sorghum, millet, triticale etc. Exemplary "starch containing grains" from seeds or "pseudocereals" include, but are not limited to e.g., quinona, buckwheat, amaranth, etc. Exemplary "starch containing grains" from oilseeds include, but are not limited to e.g., soybeans, flax, sunflower, cottonseed, camelina, etc. Indeed, soybeans and soybean meal prepared using methods disclosed herein provide a high quality soy protein wherein anti-nutritional oligosacharides and phytate are reduced or eliminated by comparison to soy protein meal prepared by mechanical methods.

The term "oilseed" as used herein, refers to seeds comprising a relatively high oil content such that they can readily be processed to provide vegetable oil. Although oilseeds e.g., soybeans, canola, sunflower, flax, etc, are commonly used in the production of vegetable oils, oilseeds also comprise carbohydrates in the form of starch or simple sugars and thus are a "starch containing grain" as defined herein. As such they are suitable for use in preparing a plant protein concentrate.

The term "starch" as used herein refers to a carbohydrate compound having the formula $(C_6H_{10}O_5)_n$, where the subscript "n" denotes the total number of glucose monomer units. Typically, starches comprise the polysaccharides amylose and amylopectin. The amylose polysaccharide is comprised primarily of glucose monomer units joined to one another in $\alpha$-1,4 linkages. Amylose is typically considered a linear molecule, however some minor branching sometimes is found. Typically, amylose polymers range in length from between about 500 to about 20,000 glucose monomer units, but any length is possible. Amylopectin is also comprised of glucose monomer units, but is not usually considered to be a strictly linear molecule. Instead, the polysaccharide comprises $\alpha$-1,4 linked glucose monomers interspersed at intervals with branches formed by glucose monomers in $\alpha$-1,6 linkage (see e.g., Advances in Food and Nutrition Research, Vol. 41: *Starch: Basic Science to Biotechnology*, Mirta Noemi Sivak and Jack Preiss eds. Academic Press (1998) which is incorporated herein by reference in its entirety).

The relative content of amylose and amylopectin in starch can vary. Typically, amylose comprises about 20% to about 25% to about 30% of the starch, but may be present in higher concentrations as well. For example "high-amylose corn starch" (HACS) comprises at least about 40% amylose, and in some embodiments comprises about 50%, about 55%, about 60%, about 65%, about 70%, about 75% amylose, and in other embodiments comprises about 80% amylose or about 85% amylose. Amylopectin on the other hand, typically comprises about 70% to about 75%, to about 80% of the starch, but may occur in higher proportions or lower proportions as well, e.g., waxy corn starch may comprise more than 99% amylopectin, and HACS may comprise as little as 15% amylopectin or less.

Starch is found in nearly every type of plant tissue including, but not limited to the fruit, seeds, stems, leaves, rhizomes and/or tubers. Thus, many starches are plant derived starches or "plant starch". Typically, starch produced in the USA is derived from corn, potatoes, rice, and wheat. However, useful starches can come from any source e.g., seaweed and other macroalgae, uni-cellular micro-algaes; arrowroot; guar gum; locust bean; tapioca; arracacha; buckwheat; banana; barley; cassava; konjac; kudzu; oca; sago; sorghum; sweet potato; taro; yams; soybeans; and beans e.g., favas, lentils and peas.

The term "starch" as used herein, also refers to "modified starch" which has been modified by human intervention such that it differs from the raw, unmodified form as extracted from a plant. For example, starch can be modified by methods known in the art such as e.g., by inter alia chemical crosslinking and/or by stabilization through the introduction of anionic groups to the starch granule.

The term "aquaculture" as used herein, refers to the farming of aquatic organisms e.g., fish, mollusks, crustaceans etc, with some sort of intervention in the rearing process to facilitate production, e.g., regular stocking, feeding, protection from predators, etc.

The term "slurrying" as used herein, refers to combining a solid or semi solid substance with a liquid and mixing to form a more or less homogeneous mixture. Thus, the phrase "slurrying the ground starch containing grain" refers to mixing the ground starch containing grain e.g., barley, with a liquid e.g., water, to form a more or less homogeneous mixture.

The term "fermentation" as used herein refers to the conversion of a "fermentation substrate" e.g., a carbohydrate e.g., a starch, sugar, etc, into a "fermentation product", e.g., an acid or an alcohol. In an exemplary embodiment, fermentation utilizes a fungus to convert a sugar into an alcohol. In another exemplary embodiment, fermentation utilizes a bacterium to convert a sugar into an acid. In another exemplary embodiment, fermentation is carried out in an anaerobic environment. In still another exemplary embodiment, fermentation is carried out in an aerobic environment.

The term "fermentation organism" as used herein, refers to any organism which, under appropriate conditions e.g. anaerobic conditions, is capable of fermenting a fermentation substrate e.g. glucose. In an exemplary embodiment a fermenting organism is a fungus e.g., *Saccharomyces cerevisiae, Pichia stipitis, Rhizopus oryzae, Rhizopus microsporus*. In another exemplary embodiment, a fermenting organism is a bacterium e.g. *Zymomonis mobilis*.

The expression "fermenting until fermentation is complete" as used herein, refers to fermenting until at least most of the fermentation substrate has been converted to fermentation product.

The expression "drying at a temperature below that which would denature or damage proteins" as used herein, refers to temperatures which are lower than those which are known to cause proteins to become denatured. In an exemplary embodiment a "temperature below that which would denature or damage proteins" is a temperature that is below about 100° C., e.g., about 20° C., about 25° C., about 30° C., about 40° C., about 50° C., about 60° C., about 70° C., about 80° C., or about 90° C. In another exemplary embodiment, a "temperature below that which would denature or damage proteins" is a temperature that is in a range that is between about 40° C. and about 100° C. Thus, in some exemplary embodiments, a "temperature below that which would denature or damage proteins" is a temperature that is about 40° C., about 50° C., about 60° C., about 70° C., about 80° C., about 90° C., or about 100° C.

The term "fermentation product" as used herein, refers to a substance or product that is produced by fermentation. In an exemplary embodiment a fermentation product is an alcohol e.g., ethanol, methanol, butanol. In another exemplary embodiment, a fermentation product is an antibiotic e.g., penicillin. In another exemplary embodiment a fermentation product is an amino acid. In another exemplary embodiment, a fermentation product is an organic acid e.g., lactic acid, acetic acid, citric acid.

The term "beta glucan" as used herein refers to a carbohydrate compound having the formula $(C_6H_{10}O_5)_n$, where the subscript "n" denotes the total number of glucose monomer units with the glucose monomer units linked by beta 1,3 linkages.

I. Introduction:

In an exemplary embodiment, the invention provides a process for producing a protein concentrate from a starch containing grain. Thus, in an exemplary embodiment, the invention provides a high quality, highly digestible protein concentrate that, in an exemplary embodiment, is suitable for use in the preparation of aquaculture feeds.

In an exemplary embodiment, the process is optimized for protein production and utilizes hulless grains. Typically, the hulless grains are ground, mixed with water to produce a mash, which may then be processed according to either a cooked or no-cook process.

The mash is enzymatically treated to hydrolyze starch and beta glucans (if present) thereby freeing insoluble proteins and producing fermentable sugars, primarily glucose. Either simultaneously, or subsequently, the enzymatically treated mash is fermented to produce ethanol. After fermentation, but prior to distillation, the liquid fraction, and solid fraction which comprises the protein, are separated e.g., by centrifugation. The protein containing solid fraction is dried at temperatures not exceeding 100° C. In an exemplary embodiment, the liquid fraction is used as a fermentation feedstock for ethanol production. In another exemplary embodiment, the liquid fraction is used for the production of other fermentation products e.g., methanol, citric acid, amino acids, etc. Thus, the process produces a fermentation feedstock, and also a protein concentrate, wherein the protein comprising the protein concentrate is a high quality, highly digestible protein suitable for use in aquaculture feeds.

II. Production of Protein Concentrate

A. Grains

Barley

Barley is a short-season, early maturing crop that is grown commercially in both irrigated and in dry land environments. Barley is resistant to drought, flood and frost is thus adapts well to many different types of growing environments. Because of its adaptability and the ability to tolerate a wide range of environmental conditions, barley can be grown in many regions of the world where it may be difficult or impossible to grow other types of cereal grain.

In an exemplary embodiment, the process disclosed herein for producing a protein concentrate utilizes barley as a starch containing grain. Any barley variety e.g., hulled or hulless (see e.g., Cereal Chemistry 76: 589-599) can be used.

In one exemplary embodiment, the process utilizes a hulled barley variety. "Hulled" or equivalently "covered" barley varieties produce kernels with a tough inedible outer hull. Typically, the tough outer hull or husk is removed before use in the methods disclosed herein. "Dehulled barley" is prepared by any method known in the art (e.g., using a vertical sheller) and refers to barley kernals that have had their outer hull removed, but which still have the germ and the outer layer of bran. Thus, in one exemplary embodiment, hulled barley kernals are first dehulled using standard techniques well known in the art.

"Dehulled" barley can be further processed to remove the bran layer and thereby provide a further dehulled barley referred to in the art as "pearled barley". In one exemplary embodiment, "pearled barley" is processed by the methods disclosed herein. However, in this embodiment, the pearling process removes some of the protein that could otherwise be recovered using the methods disclosed herein.

Although Hulled barley is typically dehulled, in one another exemplary embodiment, "hulled barley" is processed according to the methods disclosed herein without removing the tough outer hull or husk. In this embodiment, a more fibrous protein concentrate is obtained.

In one exemplary embodiment, the barley is a hulless variety of barley. Hulless barley is typically used without dehulling prior to use. In one exemplary embodiment, the hulless barley variety is Merlin.

Thus, barley processed as disclosed herein, is a useful source of plant protein for use in aquaculture feeds. Indeed, as disclosed in e.g., Example 6, barley protein concentrate prepared as disclosed herein is palatable to fish e.g., trout. Furthermore, barley protein concentrate prepared as disclosed herein supports growth rates of trout comparable to fishmeal based feeds see e.g., Example 7.

Other Starch Containing Grains

Other grains can be used to prepare protein concentrates by the disclosed processes. In one exemplary embodiment the starch containing grain is oats. Indeed, in an exemplary embodiment, oat protein concentrate having at least about 47% protein concentration is prepared according to the process.

In another exemplary embodiment, the starch containing grain is wheat. In an exemplary embodiment, wheat protein concentrate containing at least about 31% protein is prepared according to the process.

In still another exemplary embodiment, the starch containing grain is soy beans. Soy protein concentrate prepared according to the methods disclosed herein is typically free of the anti-nutritional oligosaccharides and phytate that comprise soybean meal and soybean concentrates produced by other methods. Without being bound by theory, it is believed that enzymatic action of selected fermentation microbe/microorganism that are used in the process is responsible for the elimination/reduction of phytate and anti-nutritional oligosaccharides. Exemplary microbe/microorganism whose use in the process results in a reduction/elimination of phytate include e.g., *Rhizopus oryzae* and *Rhizopus oligosporus*. In addition to eliminating certain anti-nutritional compounds from soy protein concentrates, the disclosed methods provide a soy protein concentrate which has a higher protein concentration than that of typical soy meal. Indeed, soy protein concentrate prepared according to the methods disclosed herein typically comprises between about 54% to about 62% protein. In an exemplary embodiment, a soy protein concentrate containing about 57% protein is prepared according to the process.

Although methods that employ mechanical fractionation can produce soy protein concentrates containing 70% protein, it has not been heretofor been appreciated that an enzymatic/biological process could produce a soy protein concentrate having a high concentration (typically between about 54% to about 62%) of protein. Since the biological process disclosed herein is less expensive than other methods known in the art, the process disclosed herein provides high protein soy protein concentrate at reduced cost.

In general, any starch containing grain or oil seed e.g., barley, wheat, corn, triticale, milo (grain sorghum), oats, rye, millet, soybeans, etc, can be used to prepare a protein concentrate according to the process for preparing a protein concentrate disclosed herein.

B. Preparation of Starch Containing Grains

Dehulling

In one exemplary embodiment the disclosed process for producing a protein concentrate incorporates a dehulling step. In one exemplary embodiment, dehulling utilizes standard, commercially available dehulling equipment (see e.g., R. D. Reichert et al. (2006) Journal of Food Science 49(1): 267-272).

Any milling method that removes and separates the hull from the rest of the grain is suitable for use in the methods disclosed herein. In an exemplary embodiment, dehulling is accomplished in a mill using rotating abrasive stones, resistance bars and screen. The hull and dust from the milling process are removed by screening and vacuum to dust collectors. As the skilled artisan will appreciate, the degree of dehulling or pearling is a function of the clearance, speed and grit of the abrasive stones.

Although starch containing grains can be processed to provide a protein concentrate without first dehulling the grain, dehulling removes fiber that would otherwise end up in the protein concentrate. In an exemplary embodiment, a protein concentrate prepared according to the methods disclosed herein is use for the preparation of an aquaculture feed. Since fiber is typically indigestible in fish, it is desirable to dehull the starch containing grain e.g., barley kernels, at least to a degree wherein the hull (husk) is removed and the bran is left attached to the kernel, prior to preparing a protein concentrate for use in aquaculture feeds.

In one exemplary embodiment, dehulling removes between at least about 60% to about 100% of the hull from the grain. In another exemplary embodiment, dehulling removes at least about 75% of the hull from the grain. In another exemplary embodiment, dehulling removes at least about 85% of the hull from the grain. In still another exemplary embodiment, dehulling removes at least about 95% of the hull from the grain.

In another exemplary embodiment, the disclosed process for producing a protein concentrate utilizes a hulless grain variety, e.g., a hulless barley variety, thereby obviating a dehulling step.

Grinding

Any method known in the art which will reduce particle size of the grain can be used for grinding the starch containing grain or oil seed. In one exemplary embodiment particle size of the grain is achieved by use of a hammermill. In another exemplary embodiment particle size of the grain is achieved by use of a roller mill. Hammermills and roller mils are well known in the art (see e.g., Kim Koch, *Hammermills and Roller mills*, Kansas State University, May 2002).

In one exemplary embodiment, a standard hammer mill is operated with a screen size to mill grain to wherein at least about 50% or more of the ground grain will pass a 20 mesh US standard screen. However, in some exemplary embodiments, a coarser ground grain is used. In one exemplary embodiment, a standard hammer mill operated with a screen size to mill grain to wherein at least about 50% or more of the ground grain will pass a 16 mesh US standard screen. In other exemplary embodiments a course ground grain wherein at least about 50% or more of the ground grain will pass a 10 mesh US standard screen is used. In still other exemplary embodiments, a very fine ground flour is used e.g., wherein at least about 50% or more of the ground grain will pass a screen with smaller openings than a 20 mesh US standard screen.

C. Processing Grains to Prepare a Grain Slurry

A grain slurry is typically prepared from the starch containing grain. Typically, ground starch containing grain is slurried with water to a total solids content of between about 10% to about 40%. The protein concentrate is prepared from the slurry using one of several process options disclosed herein below.

Mash Solids Content

In an exemplary embodiment, mash is prepared with as high a solids content in the mash as possible without reducing product yield or conversion efficiency. Typically, mash viscosity is the factor limiting the maximum percent solids in the mash and solids content will vary with grain; e.g., barley typically makes a more viscous mash than corn. In general, viscocity of the mash has an upper range of between about 2500 centipoides (cp) to about 5000 cp. The skilled artisan will appreciate the appropriate solids content for their particular application.

In one exemplary embodiment, a barley mash is prepared which comprises a solids concentration of about 35%, w/v in water. In another exemplary embodiment, the maximum that can be achieved with effective agitation and heat transfer using the available equipment. Typically the range for barley mash is between about 10% to about 40% w/v. With starch containing grains other than barley, solids content is typically between about 10% to about 50% w/v.

Fortunately however, total solids content can be higher than about 40% in the case of barley, or higher than 50% in the case of other starch containing grains when a fed batch system is used to prepare the mash. Indeed, in one exemplary embodiment, a fed batch system is employed to provide a barley mash comprising about 60% w/v solids content. Without being bound by theory, it is believed that more starch containing grain e.g., barley can be added as starch is converted to soluble sugars and alcohol. In fed batch systems, enzymatic hydrolysis reduces viscosity, thereby permitting additional grain to be added to the mash.

D. Processing Slurried Mash

1. Cooking Process

In one embodiment the slurry is adjusted to pH 5 to 7. The slurry is then heated and held at a temperature that is between about 80° C. to about 125° C. for 5 minutes to 24 hours. Any means of heating and holding the slurry known in grain processing may be used e.g., batch tanks heated by steam injection or heat exchangers, jet cookers, hydroheaters feeding into holding tanks, etc. A heat tolerant alpha amylase (e.g., from *Bacillus licheniformis*) is added in an amount sufficient to hydrolyse the starch to soluble dextrins. Methods for measuring soluble dextrins are well known in the art (see e.g., L. Serre and C. Laurière (1990) Analytical Biochemistry 186 (2):312-315).

The heat tolerant alpha amylase alpha amylase can be any commercially available, heat tolerant alpha amylase and is typically used as recommended by the manufacturer. In one exemplary embodiment, the heat tolerant alpha amylase is Termamyl® SC from Novozymes is added in an amount equal to 0.025 to 0.05% of the weight of grain. Fermentation samples can be analyzed to determine the amount and composition of remaining starch to establish a baseline consistent with time or viscosity.

After heating, the slurry is cooled to at least about 70° C. or less, and pH adjusted to a pH that is between about pH 5 to about pH 7. Glucoamylase is added to the cooled cooked mash in an amount sufficient to hydrolyse the soluble dextrins to glucose. Glucoamylase can be any commercially available or in house produced, glucoamylase. Commercially available glucoamylase is typically added at a temperature and in an amount in accordance with manufacturer's recommendations. In an exemplary embodiment, the glucoamylase Spirizyme® fuel from Novozymes is added in an amount equal to 0.04 to 0.06% of the weight of grain.

In some exemplary embodiments, the starch containing grains e.g., barley, comprise beta glucans. Thus, in some exemplary embodiments, beta glucosidase enzymes are also added. In general, beta glucosidase is added in an amount and under conditions of temperature and pH consistent with manufacturer's recommendations such that it is sufficient to hydrolyze essentially all of the beta glucans present. Methods for measuring beta glucans are known in the art (see e.g., Maximov, V. I. et al. (1975) Prikl Biokhim Mikrobiol. 11(3): 455-459, EP0709681, etc). In an exemplary embodiment, the beta glucanase Viscozyme® L from Novozymes is added in an amount between 0.1 and 0.3% of the weight of grain.

The slurry comprising the glucoamylase and beta glucanase enzymes is typically held at a temperature of between about 35° C. to about 70° C. for a period of up to about 12 hours and cooled to 20° C. to 35° C., or until a viscosity range of about 100 cp to about 1000 cp is obtained. A viscosity of 100-1000 cp is an indicator that all the starch has been converted to sugar. Cooking and enzymatic hydrolysis of starch to glucose can also be monitored by assaying for glucose by any standard assay method such as e.g., high performance liquid chromatography. Glucanase and beta glucosidase enzymes can be any commercially available preparations e.g., enzyme preparations from Novozymes or Genencore. Typically, the amount of enzyme used is estimated based on the solids loading and starch/glucan content of the starch containing grain e.g., barley. In general, the enzyme dosage is chosen such that it is sufficient to solubalize essentially all of the starch and glucans. Thus, a person of skill in the art will thus appreciate the appropriate enzyme dosage for their particular application.

Mash Cooking

In mash cooking, any system that increases the mash temperature to at least the gelatinization point of the grain starch is suitably employed. Typically, gelatinization temperatures for starch vary depending on the type and source of starch and can be determined by any method known in the art (see e.g., Li F.-D.; et al. (2004) J. Food Eng. 62(2):113-120). Most grain derived starches typically begin gelatinization around about 65° C., where as potato starches typically begin gelatinization at temperatures of around about 51° C. In the cooking process, the range of temperatures can vary from 65° C. to 140° C. The preferred temperature range for our process is 90° C. to 120° C. The temperature range is high enough to impede or kill off contaminating microbes, the amylase enzymes still work, but low enough that the protein molecules aren't altered. In the "no-cook" process, it is not necessary to heat the starch to gelatinization temperatures.

Cooking systems can be batch tanks or continuous flow using "jet cookers". In an exemplary embodiment, a commercial scale process employing barley is cooked with a jet cooker of the type routinely employed in dry mill ethanol production. The jet cooker is operated to achieve 80° C. to 120° C. and to feed a holding tank or vessels to hold 80° C. to 100° C. for at least 1 hour. Process development employed a batch tank fitted with steam coils for heating and agitation that cooked the mash at 90° C.

Enzymatic Liquefaction of Cooked Mash

In one exemplary embodiment, a temperature and acid tolerant alpha amylase is used to solubalize and/or liquefy gelatinized starch. Temperature and acid tolerant alpha amylase enzymes typically tolerate up to 110° C. and typically have pH optima in the range of about 4 to about 6. Some exemplary temperature and acid tolerant alpha amylase enzymes suitable for use with cooked grain mash include, but are not limited to Genencor SPEZYME FRED, Novozymes Liquozyme®. In one exemplary embodiment, a barley mash is pH adjusted to about pH 5 and the mash is heated to a temperature that is an range that is between about 90° C. to about 105° C., and alpha amylase is added at a ratio of enzyme to starch that matches the manufacturers recommendation for dose rate. Any alpha amylase enzyme may be used in the process, including enzyme prepared by culture of a selected microorganism in a separate but parallel process on site or elsewhere (see e.g., W/O 1989/012679; U.S. Pat. No. 4,536, 477; Aehle, Wofgang ed. Enzymes in Industry: Production and Applications. Wilet-VCH, 2007) or alpha amylase purchased from commercial suppliers.

Enzymatic Saccharification of Cooked Liquefied Mash

In one exemplary embodiment, a glucoamylase with activity up to 70° C. is used. In an exemplary embodiment, Genecor Distillase or Novozymes Spiritzyme are a commercially available glucoamylases suitable for use in the process. In one exemplary embodiment, a cooked barley mash is cooled to about 65° C., pH adjusted and enzyme added at a dose rate consistent with the manufacturer's recommendation. The mash is held for a period of between about a few minutes to about 24 hours at a temperature of between about 50° C. to about 70° C. then cooled to fermentation temperature of 20° C. to 35° C. Any glucoamylase may be used in the process including glucoamylase produced by a selected microorganism in a separate parallel process at the site of protein production or elsewhere, using methods known in the art (see e.g., U.S. Pat. No. 4,536,477).

Beta Glucan Hydrolysis

In one exemplary embodiment, the process utilizes barley and employs a beta glucanases to hydrolyze the beta glucans in barley to glucose. Beta glucan hydrolysis reduces viscosity, solubalizes carbohydrate thereby increasing protein concentration and ethanol yield. Beta glucanases are added at the temperature an pH recommended by manufacturers. Exemplary beta glucanases include, but are not limited to Genencor Optimash and Novozymes Viscozyme. However, any beta glucanase may be used in the process including beta glucanase produced by a selected microorganism in a separate parallel process at the site of protein production or elsewhere as is known in the art. In one exemplary embodiment, beta glucanase is added after cooked mash is cooled to the appropriate temperature. In another exemplary embodiment, beta glucanase is added to the mash prior to cooking to reduce mash viscosity.

Fermentation of Cooked, Saccharified Mash

After addition of glucoamylase and beta glucanase, mash is further cooled to 35 C and yeast culture is added to initiate fermentation. In an exemplary embodiment, fermentation temperature is about 35° C. In another exemplary embodiment, fermentation temperature is in a range that is between about 15° C. to about 40° C. In one exemplary embodiment, pH is about 4.0. In other exemplary embodiments pH varies within a range that is between about 3.3 to about 7.

In some exemplary embodiments, the fermentation organism is a yeast that produces ethanol from glucose e.g., Saccharomyces cerevisiae (see e.g., Frelot, D., et al. (1982) Biotechnology Letters 4(ii):705-708). In some exemplary embodiments, the fermentation organism is bacteria that produces ethanol or other fermentation products from glucose e.g., Zymomonas. In one exemplary embodiment, yeast with rapid fermentation and tolerance up to 12% w/w ethanol in the fermentation beer is used. Typically, yeast are prepared in an inoculum culture approximately 1% of the mash volume. Inoculum culture is grown in a nutrient broth for 24 hours to a cell density of about 100 million per ml. When added to the saccharified mash, the initial yeast cell density is typically about one million per ml. However, a wide range of yeast strains and inoculum procedures may be used in the process provided that the selected yeast and inoculum procedure results in an acceptable conversion of glucose to ethanol. In one exemplary embodiment, fermentation is inoculated directly with commercially available dried yeast preparations. Fermentation is maintained at 15° C. to 40° C. or preferably 35° C. until maximum conversion of glucose and other fermentable sugars to ethanol is complete. Fermentation completeness can be monitored by methods know to the art e.g., by sampling and assay of ethanol concentration (see e.g., Hyun-Beom Seo et al. (2009) J. Ind. Microbiol. Biotechnol. 36:285-292) or by assay for residual starch and soluble sugars (see e.g., Vidal, Bernardo C. et al. (2009) Cereal Chemistry 86(2):133-135; Saglio, P. H and Pradet, A. (1980) Plant Physiol. (1980) 66:516-519) in the fermented mash. Fermentation time will vary with initial grain solids loading and available starch content. In an exemplary embodiment, barley at 35% solids, to a final fermentation ethanol concentration of 8 to 12% w/w fermentation time is 48 to 60 hours.

Range of fermentation time typically varies from between about 8 to about 72 hours. In some exemplary embodiments, the organism added to the cooked saccharified mash is a fungus e.g., *Rhizopus* that converts sugars to cell mass which increases protein production or protein concentration.

2. No Cook Process

In one exemplary embodiment, the invention provides a process for hydrolysis of grain starch and fermentation of sugars is a no cook process. In a no-cook process, temperature of the mash is kept temperatures below the gelatinization point for the starch. No-cook processes are known in the art (see e.g., U.S. Pat. No. 7,037,704; U.S. Patent Application Publication 20040234649; U.S. Patent Application Publication 20050233030; U.S. Patent Application Publication 20040219649). In one exemplary no cook process, barley mash is prepared comprising about 10% to about 35% solids (w/v). The mash is adjusted to a pH between about 3.5 and about pH 4.0 followed by the addition of yeast culture and an enzyme preparation that hydrolyzes ungelatinized raw starch. In an exemplary embodiment, an enzyme preparation comprising alpha amylase and beta glucanase is suitable for this process. In another exemplary embodiment commercially available enzyme preparations may also be used in a no cook process at temperatures below the gelatinization point for the starch. Mash with enzyme and yeast is incubated, preferably with agitation, at a temperature that is a member selected from a temperature that is between about 30° C. to 70° C. for about 48 hours to about 72 hours in a simultaneous starch hydrolysis and fermentation.

E. Processing the Fermented Slurry to Prepare a Protein Concentrate

Solids Liquid Separation

After fermentation is complete and prior to distillation, solids are separated from the liquid by processes known in the art e.g., centrifugation, filtration, etc. In one exemplary embodiment, a Sharples continuous flow centrifuge is used. However any suitable centrifuge or filter system may be employed. The liquid stream is distilled to recover the ethanol. In one exemplary embodiment, distillation bottoms or liquid remaining after ethanol is removed may be recycled back for use as "backset" or the make up water to form the mash.

Soluble protein is recovered e.g., from distillation bottoms, by any known processes e.g., evaporation, and added to the solids. Solids from the separation are dried in air at temperatures of less than about 100° C. in the solids. In some exemplary embodiments, Solids from the separation are dried in air at temperatures in a range that is between about 40° C. to about 100° C. However any temperature that will not denature or damage the protein is suitable. The dried solids are ground to a powder using a hammer mill or other suitable equipment to form the grain protein concentrate.

In one exemplary embodiment, the resulting protein concentrate is a barley protein concentrate comprising at least about 53% protein. In another exemplary embodiment, the resulting protein concentrate is a barley protein concentrate wherein the protein concentration is selected from protein concentrations in a range of between about 30% protein to about 70% protein.

In one exemplary embodiment, the protein concentrate has greater than 80% protein digestibility, phosphate availability of about 70%, is palatable to trout and thus, is used as one of the protein ingredients in trout feeds.

In other exemplary embodiments other grain protein concentrates are prepared according to the processes disclosed herein and the protein concentrates comprise protein in a concentration selected from protein concentrations in a range of between about 36% protein to about 75% protein and are suitable for use in aquaculture feeds.

Variations

In one exemplary embodiment, the solid and liquid fractions are separated before fermentation by mechanical means such as by centrifuge or by filtration. The damp solids fraction is collected, reslurried in water to wash our residual sugars and reseparated by centrifuge or filtration. The solids are recovered and dried. The solids fraction is the protein concentrate and typically comprises between about 30% protein and about 70% protein. The liquid fraction is fermented by addition of a fermentation organism as disclosed herein above and then distilled.

In another exemplary embodiment, the solids and liquid fraction are separated before fermentation by mechanical means such as by centrifuge or by filtration. The moist solids are inoculated with a fungal culture. Without being bound by theory it is believed that the innoculated fungi utilize the residual sugars and thus, remove the sugars from the protein concentrate. After a suitable culture period that is typically between about 24 hours to about 72 hours, the solids are dried and ground to prepare the protein concentrate. The liquid stream is fermented to ethanol or other product. Because the fungus more efficiently removes soluble sugars, this embodiment does not utilize a wash step therefore, the liquid stream to fermentation is not diluted and can be processed more efficiently.

Suitable fungi for innoculation of the moist solids include, but are not limited to any fungus that it is a fungus that utilizes sugars and is non toxic and non pathogenic and safe to use in animal feeds. Additionally, in an exemplary embodiment, the fungus is palatable to the fish or animals. In one exemplary embodiment, the fungus is *Rhizopus oryzae*. In another exemplary embodiment, the fungus is and *Rhizopus microsporus*. Typical protein concentrations using this approach are about 60%.

In another exemplary embodiment, soluble protein in distillation bottoms is recovered by culturing a yeast or fungus in the distillation bottoms. Sugar or hydrolyzed grain mash is added in an amount that is between about 0.5 to 1% to provide a carbon source. The microorganism utilizes the soluble protein and any added sugar, converting the nutrients to insoluble cell mass which is recovered by filtration or centrifugation and add to the solids. Any yeast fungus can be used provided that it is a fungus that is non toxic and non pathogenic and safe to use in animal feeds; is palatable to the fish or animals and which preferentially utilizes sugars. *Rhizopus oryzae* or *Rhizopus microsporus* are two organisms suitable for this embodiment.

In still another exemplary embodiment, yeast or other fermentation organism is added to the slurry prior to solid liquids separation. The fermentation proceeds until all of the soluble sugars are converted to ethanol or other fermentation product. Typically in about 24 to about 72 hours. When the fermentation is complete, solids and liquids fractions are separated by centrifuge or filtration or other suitable means. The solids are recovered and dried. In the drying step any residual ethanol or other volatile fermentation product evaporates. The liquid fraction is sent to distillation or other fermentation product recovery step. This differs from a conventional ethanol process in that solids are separated prior to distillation. Distillation may denature or alter protein making the protein less digestible.

In another exemplary embodiment, soluble sugars in the slurry are converted to additional protein rather than to ethanol by addition of an appropriate microbe. Soluble sugars are converted to cell mass by addition of a suitable yeast or fungus grown under conditions of agitation, aeration, temperature and pH designed to produce the maximum cell mass. Cell mass is recovered together with the grain solids resulting in an increase in protein concentrate recovered from the process. Appropriate microbes include, but are not limited to any fungus or yeast that is non toxic and non pathogenic and safe to use in animal feeds; is palatable to the fish or animals and which preferentially utilizes sugars. Exemplary appropriate microbes include e.g., *Rhizopus oryzae, Rhizopus microsporus.*

In one exemplary embodiment, at least one *Rhizopus* species is added to increase protein concentration of the final protein concentrate. Typically, *Rhizopus* is added in any one of three ways to increase protein concentration. In one exemplary the *Rhizopus* is added after yeast fermentation, but before distillation to utilize soluble proteins and increase recoverable protein. In another exemplary embodiment, the *Rhizopus* is added instead of a another fungus e.g., a yeast e.g., *Saccharomyces cereviceae*. In this embodiment, the *Rhizopus* utilizes soluble sugars and soluble protein to produce cell mass instead of ethanol, increasing total protein recovery. In still another exemplary embodiment, the ground starch containing grain is slurried and the starch and glucans are solubilized with enzymes. Yeast are then added to the liquid fraction to ferment the soluble sugars to ethanol. *Rhizopus* is added to the moist solids fraction from the centrifuge prior to drying. The moist solids contain sugars which are converted to cell mass by the *Rhizopus*. In an exemplary embodiment, the starch containing grain used for this embodiment, is soybeans. In this embodiment, fermentation with the *Rhizopus* reduces or eliminates phytate and other anti-nutritional compounds typically associated with soybeans, and so provides a protein concentrate with reduced or eliminated phytate and reduced or eliminated anti-nutritional factors.

In all embodiments, drying steps are conducted at temperatures below the point where proteins are denatured, burned or otherwise adversely altered. In one exemplary embodiment air drying at about 50° C. is used. In another exemplary embodiment air drying at or below 50° C. is used.

Typically, in the protein concentrate is a fine brown to off-white powder comprising between about 30% to about 70% or more protein. In one exemplary embodiment, the protein concentrate comprises about 35% protein. In another exemplary embodiment, the protein concentrate comprises about 40% protein. In another exemplary embodiment, the protein concentrate comprises about 45% protein. In another exemplary embodiment, the protein concentrate comprises about 50% protein. In another exemplary embodiment, the protein concentrate comprises about 55% protein. In another exemplary embodiment, the protein concentrate comprises about 60% protein. In another exemplary embodiment, the protein concentrate comprises about 65% protein.

III. Aquaculture

As noted above aquaculture is the fastest growing food production sector in the world. For example, the current value of US aquaculture production is near $900 million annually, the US Department of Commerce hopes to increase this to $5 billion by 2025. Thus, Aquaculture is truly the next agricultural revolution because of the great changes it is generating in the production of shellfish and finfish products.

For aquaculture to continue its growth, improved sources of plant based protein, are needed. A primary objective in diet formulation for fish is to provide a nutritionally balanced mixture of ingredients to support the maintenance, growth, reproduction, and health of the animal at an acceptable cost. Many of the nutrient requirements of fish and aquaculture nutrition are known in the art see e.g., *Nutrient Requirements of Fish*, Committee on Animal Nutrition, Board on Agriculture, National Research Council, NATIONAL ACADEMY PRESS, Washington, D.C. 1993 National Academy of Sciences 1. Aquaculture Feed Processing As is well known in the art, fish feeds are typically processed into water-stable, particulate forms (granules, pellets) for efficient consumption by the fish and to minimize fouling of the water. Most manufactured fish feed is processed by compression pelleting or extrusion; other manufactured forms include moist (or semimoist), microencapsulated, and micropulverized feeds. These processes are well known in the art.

Fish meal has been a primary protein source in trout feeds and any changes that can reduce fish meal levels and total costs are beneficial. Replacing fish meal with plant protein is a first step, but amino acid content of plant based diets can be limiting. Amino acids are needed for many metabolic functions, the largest being protein accretion and metabolic fuel. Providing the proper dietary amino acid balance will reduce feed costs and nitrogenous waste output as ammonia.

Complete replacement of fish meal protein with plant protein without a reduction in growth has been the goal of many studies (see e.g., Adelizi P. D., et al, supra). However, as is known in the art, protein source affects growth rate (see e.g., F. T. Barrows, et al. (2007) Aquaculture Research 38 (16): 1747-1758).

Feed acceptability, palatability and digestibility vary with the ingredients and feed quality. Fish farmers pay careful attention to feeding activity in order to help determine feed acceptance, calculate feed conversion ratios and feed efficiencies, monitor feed costs, and track feed demand throughout the year.

Published feeding rate tables are available for most commonly cultured fish species. Farmers can calculate optimum feeding rates based on the average size in length or weight and the number of fish in the tank, raceway, or pond by methods known in the art (see Hinshaw 1999, and Robinson et al. 1998). Farmed fish typically are fed 1-4% of their body weight per day depending on fish size, water temperature and species.

2. Aquaculture Feeding Practices

Typically, different sizes and species of fish and the diverse environmental and management conditions used in aquaculture require different feeding strategies. Diet characteristics, such as source (living or nonliving feed), particle size, texture, density, and palatability, must be carefully considered for size and species of fish. Feed allowance and frequency of feeding are important for growth rate and feed efficiency. Type of feed (floating or sinking) used and method of feeding will depend on the fish, the culture system, and the equipment and personnel available.

IV. Other Uses of Protein Concentrate

The protein concentrate produced by methods disclosed herein is suitable for use as an ingredient in aquaculture feed and in other animal feeds where a plant-derived, high protein source is needed or desired.

A. Ethanol Production

Ethanol is produced from the liquid fermentation stream by methods known in the art (see e.g., Gyamerah, M. and Glover, J. (1996) J. of Chem. Tech. and Biotech. 66(2):145-152; Minier M. and Coma, G (1981) *Biotechnology Letters* 3(8): 405-408; P. Christen et al. (1990) Biotechnology and Bioengineering 36(2):116-123). In one exemplary embodiment, the liquid stream and the wash water are combined in an appropriate tank. A suitable fermentation organism is added and the liquid stream fermented. Exemplary suitable organisms include, but are not limited to yeasts which ferment the liquid stream to ethanol. Ethanol concentration in the fermented liquid typically depends on the solids content of the original slurry and the carbohydrate content of the barley but is typically in a range that is between about 3% to 15%. After separating the protein solids, the fermented liquid stream is distilled by known methods to separate the ethanol from the water (see e.g., Kister, Henry Z. (1992). *Distillation Design* (1st Edition ed.). McGraw-Hill).

The following examples are offered to illustrate, but not to limit the invention.

EXAMPLES

Example 1

The following example illustrates an exemplary process by which a protein concentrate was produced at pilot scale from barley.

Hulless barley, Merlin variety, was ground in a hammer mill using a fine screen. Ground barley was mixed with water to make a mash with 20% solids content in a 300 liter batch tank equipped with agitation and heat exchanger. The pH was approximately 5.5. Mash heating was initiated and when the mash reached 50° C., alpha amylase (Genecor SPEZYME FRED) was added in the mount of 3.3 ml per kg barley. Heating continued until the mash was 90° C. Mash was held at 90° C. for two hours. Mash was then cooled to 65° C. Glucoamylase (Genencor Distillase 500 L) at the rate 1.6 ml per kg of grain and Beta glucanase (Genencor Optimash BG) was added at the rate of 1.66 ml per kg of grain. Mash cooled slowly for 16 hours to 35° C. at which time a yeast culture was added. Initial cell density was about one million yeast per ml of mash. Fermentation was maintained at 35° C. with agitation for approximately 52 hours. Fermentation beer was then centrifuged using a Sharples centrifuge operated at 70,000 rpm. Liquid stream was sampled and ethanol concentration determined by gas chromatography to be 5% w/w. Solids were recovered from the centrifuge, dried and ground. Protein concentration of the dry powder was determined as total N using a Leco nitrogen analyzer with protein concentration equal to % N×6.25. Protein concentration from 7 production batches of barley protein concentrate averaged 54% Protein concentrates prepared as in this example were used to formulate feeds for trout feeding trials as described in Examples 5 and 6.

Example 2

The following example illustrates an exemplary process by which a protein concentrate was produced at laboratory scale from oats.

Oats were ground in a hammer mill using a fine screen as disclosed in Example 1. Ground oats were mixed with water to make a mash with 20% solids content in a 300 liter batch tank equipped with agitation and heat exchanger. The pH was approximately 5.5. Mash heating was initiated and when the mash reached 50° C., alpha amylase (Genecor SPEZYME FRED) was added at the 3.3 ml per kg barley. Heating continued until the mash was 107° C. Mash was held a 107° C. for seven minutes. Mash was then cooled to 65° C. Glucoamylase (Genencor Distillase 500 L) at the rate 1.6 ml per kg of grain and Beta glucanase (Genencor Optimash BG) was added at the rate of 1.66 ml per kg of grain. Mash cooled overnight to 35° C. at which time a yeast culture was added. Initial cell density was about one million yeast per ml of mash. Fermentation was maintained at 35° C. with agitation for approximately 52 hours. Fermentation beer was then centrifuged at 70,000 rpm. Liquid stream was sampled and ethanol concentration determined by gas chromatography to be 5% w/w. Solids were recovered from the centrifuge, dried and ground. Protein concentration of the dry powder was determined as total Nitrogen (N) using a Leco nitrogen analyzer with protein concentration equal to % N×6.25.

Oats treated the laboratory scale process resulted in a protein concentrate with 47.5% protein.

Example 3

A standard hulled barley variety (Baronesse) was dehulled and treated by the process disclosed in Example 1. Except that the mash was cooked by pumping through a hydroheater at 105° C. then into a 200 gallon tank where the mash was cooled to 90° C. alpha amylase added and held for about 2 hours. Mash was further cooled to 65° C. when glucoamylase and beta glucanase were added and held for about 2 hours. Mash was further cooled to 35° C. when yeast were added. Fermentation and protein recovery were as described in example 1. Beginning protein content of the barley prior to dehulling was 15.7%, final protein content of the barley protein concentrate was 53.1%.

Example 4

The following Example illustrates a no-cook process for preparing a protein concentrate from barley The exemplary process utilizes Merlin barley. In the no cook process, a barley mash is prepared at 30 to 35% solids and is adjusted to a pH between 3.5 and 4.0 followed by the addition of yeast culture and an enzyme preparation that hydrolyzes ungelatinized raw starch. The enzyme preparation comprises a culture of a selected strain of Aspergillus grown in solid substrate culture as disclosed in co-pending U.S. patent application Ser. No. 12/264,875, filed Nov. 4, 2008 which is incorporated herein by reference in its entirety. Some suitable enzyme mixtures are also commercially available. Mash with enzyme and yeast is incubated preferably with agitation at 30° C. to 35° C. for 48 to 72 hours in a simultaneous starch hydrolysis and fermentation.

As for the "cooked" processes disclosed in Examples 2 and 3, after fermentation is complete, and prior to distillation, solids are separated from the liquid by processes known in the art e.g., centrifugation, filtration.

Solids and liquids are processed as disclosed for cooked processes.

Example 5

The following example illustrates an exemplary process by which a protein concentrate was produced at laboratory scale from soy meal. Solvent extracted soybean meal was treated in a no cook process. Ground soy meal was slurried in water to 20% solids content. The slurry was adjusted to pH 3.6 and a raw starch active amylase preparation and yeast were added. The slurry with amylase and yeast was incubated at 35° C. for 72 hours in a simultaneous hydrolysis and fermentation. The solids and liquid fractions were separated by centrifugation. The solids fraction was dried at about 50° C. and ground. The initial protein content of the soybean meal was 48%. The process yielded a protein concentrate with a final protein concentration of 57% as determined by the method of example 1.

Example 6

The following example illustrates the process for producing additional protein rather than ethanol from the soluble sugars. Hulless barley (variety Merlin) was treated enzymatically according to the methods described in example 1. When the mash was cooled to 35° C. instead of adding yeast the mash was inoculated with a culture of *Rhizopus oryzae*. The *R. oryzae* culture was prepared by transferring a storage slant culture to a nutrient broth which was grown for 48 hours. The flask culture was used to inoculate the mash at a rate of 10 ml *R. oryzae* inoculum per liter of mash. Inoculated mash was incubated at 35° C. for 72 hours. The culture was centrifuged to separate solids which were air dried at 50° C. to less than 10% moisture content. The dried solids were assayed for protein content according to the methods of example 1. Protein concentration was 58%.

Example 7

The following example illustrates a comparison of the palatability of fish meal, soy protein concentrate and a protein concentrate produced from barley according to the methods disclosed herein.

Some alternate feed ingredients adversely affect the palatability of the diet, or the willingness of fish to consume the feed. To screen ingredients for palatability prior to conducting digestibility or growth trials, a 3 week palatability trial was conducted.

Three experimental diets containing 30% of the test and control protein were fed (Table 1).

TABLE 1

Composition of diets used to determine relative palatability of protein concentrates

| Ingredient | Fish control g/100 g | Soy Control g/100 g | BPC g/100 g |
| --- | --- | --- | --- |
| Anchovy meal, 65 | 30.00 | — | — |
| Soy Protein Concentrate | — | 30.00 | — |
| Barley Protein Concentrate | — | — | 30.00 |
| Corn gluten meal | 10.37 | 10.37 | 10.37 |
| Soybean meal | 20.00 | 20.00 | 20.00 |
| Wheat gluten meal | 8.8 | 8.8 | 8.8 |
| Wheat flour | 13.06 | 13.06 | 13.06 |
| Fish oil inside | 10.53 | 10.53 | 10.53 |
| Lecithin | 2.00 | 2.00 | 2.00 |
| Di-calcium phosphate | 2.27 | 2.27 | 2.27 |
| DL-methionine | .75 | .75 | .75 |
| Lysine-HCL | 1.12 | 1.12 | 1.12 |
| Vitamin premix 30 | .80 | .80 | .80 |
| Stay-C | .20 | .20 | .20 |
| Trace mineral premix #3 | .10 | .10 | .10 |
| TOTAL | 100.0 | 100.00 | 100.00 |

The diet containing fish meal served as the positive control, and the diet containing soy protein concentrate is a plant based reference diet that has been shown to support good growth and feed consumption in long term feeding studies. Each diet was fed to triplicate tanks of 30 rainbow trout (*Oncorhynchus mykiss*) held in 75 liter tanks supplied with 14° C. water for 3 weeks, after a 2 week conditioning period.

Fish were fed by hand to apparent satiation and feed intake was monitored. After 3 weeks, feed consumption was averaged and expressed a grams feed per gram of fish weight per day. There was a significant difference in feed consumption among trout fed any of the three diets (Table 2).

TABLE 2

The effect of protein source on feed consumption

| Diet | g feed/g fish/d | % of fish control | % of plant control |
| --- | --- | --- | --- |
| Fish Control | 0.73 + 0.03 | 100.0$^a$ | 200.4 |
| Plant Control | 0.36 + 0.02 | 49.9$^c$ | 100.0 |
| Barley protein Concentrate | 0.42 + 0.03 | 56.8$^b$ | 113.8 |

As can be seen in Table 2, trout fed the plant based control only consumed 49.9% as much feed as the trout fed the fish meal control diet. Trout fed the diet containing the barley protein concentrate consumed 56.8% as much feed as the trout fed the fish meal control. The results of this trial indicate reduced feed intake of trout fed either the plant control or the diet containing the barley protein concentrate, but it is well documented that trout fed the plant control diet will adjust to the diet and after only 9 weeks of feeding. We conclude that the barley protein concentrate will not be rejected by trout in extended feeding periods and has better palatability than soy protein concentrate during the first 3 weeks of feeding.

Palatability of the barley protein concentrate is currently being conducted with a freshwater omnivore (sucker) and a marine carnivore (black sablefish).

Example 8

The following Example illustrates the digestibility of aquaculture feeds prepared with protein concentrates made according to the processes disclosed herein.

The Apparent Digestibility Coefficients (ADC) estimate the percentage of a nutrient in an ingredient that is digestible to the fish. These values are more indicative of the true nutritional value of an ingredient than chemical composition and are necessary for accurate diet formulation.

A study was conducted to determine ADC's for phosphorus, protein and amino acids. Rainbow trout (*Oncorhynchus mykiss*) (~250 g/fish) were held in 300-L fiberglass tanks and supplied with 6 l/m of 15° C. water throughout the experiment. Lighting was maintained on a 14:10 h diurnal cycle. The reference diet was composed of corn gluten meal (37.42%), wheat gluten meal (7.61%), soybean meal (20.62%), wheat flour (24.62%), lysine-HCL (1.47%), taurine (0.50%), fish oil (13.43%), stay-C (0.30%), choline-CL (0.50%), vitamin premix (0.80%), Trace mineral premix (0.10%), yttrium oxide (0.01%). Each test ingredient was mixed with the reference diet at a 30/70 ratio, w/w, before processing. The diets containing barley protein concentrates were produced by cold extrusion due to limited quantities of material available and all other diets were produced by cooking extrusion.

Diets were fed to triplicate groups of fish, and were replicated over time. Diets were randomly assigned to a tank of fish and the fish were fed to apparent satiation twice daily. The fish were fed their respective diets for seven days prior to fecal collection. Fecal samples were obtained in one collection by manual stripping 16-18 h post-feeding. Manual stripping of fish was accomplished by netting and anesthetizing all fish in the tank, followed by gently drying and then applying pressure to the lower abdominal region to express fecal matter into a plastic weighing pan. Care was taken to exclude urinary excretions from the collection. Thereafter, fish were removed, replaced with new fish, and each diet was randomly assigned to a tank of fish for the second and third replicates of diet.

$ADCN_t$=apparent digestibility coefficients of the nutrient in the test diets $ADCN_r$=apparent digestibility coefficients of the nutrient in the reference diet $a=(1-p)\times$nutrient content of the reference diet $b=p\times$nutrient content of the test ingredient $p$=proportion of test ingredient in the test diet The ADC's for protein and amino acids for the fermented BPC were very high (Table 3) and equivalent or better than standard fish meal. The ADC for protein was significantly increased by the concentration of both the washed and fermented BPC's.

TABLE 3

Apparent digestibility coefficients for phosphorus and amino acids for selected feed ingredients.

| | | | Apparent Digestibility Coefficients | | | | | | | | | | | | |
|---|---|---|---|---|---|---|---|---|---|---|---|---|---|---|---|
| | % Protein | Phosphorus | Protein | His | Gly | Thr | Ala | Arg | Tyr | Val | Met | Phe | Ile | Leu | Lys |
| Whole seed | | | | | | | | | | | | | | | |
| Barley | 14.2 | 38.6 | 56.9 | 76.5 | 60.2 | 66.3 | 63.6 | 85 | 71.4 | 74.2 | 72.0 | 81.8 | 66.8 | 77.0 | 68.1 |
| Wheat | 12.9 | 17.1 | 74.8 | 76.1 | 99.2 | 95.7 | 73.6 | 81.8 | 85.2 | 93.9 | 87.8 | 91.8 | 87.4 | 91.0 | 85.0 |
| Ethanol co-products | | | | | | | | | | | | | | | |
| BPC Washed | 54.5 | 36.5 | 79.6 | 84.3 | 79.12 | 77.4 | 66.2 | 88.6 | 80.3 | 81.3 | 83.3 | 82.9 | 81.3 | 69.0 | 81.2 |
| BPC Fermented | 57.9 | 63.7 | 90.9 | 93.3 | 91.7 | 90.9 | 82.7 | 93.5 | 91.2 | 91.6 | 92.5 | 92.3 | 92.4 | 85.0 | 93.0 |
| Air-classified barley | 25.0 | 50.7 | 92.2 | 95.3 | 91.7 | 92.8 | 90.6 | 96.8 | 90.4 | 92.5 | 92.2 | 92.5 | 86.6 | 91.6 | 87.1 |
| Fish meal | | | | | | | | | | | | | | | |
| Menhaden, Fair and Average Quality | 73.5 | 41.8 | 86.0 | 92.0 | 83.4 | 91.3 | 91.8 | 92.4 | 91.9 | 89.7 | 93.8 | 92.3 | 90.2 | 94.1 | 95.1 |

Fecal samples for a given tank were dried overnight at 50° C. and stored at −20° C. until chemical analyses were performed. Apparent digestibility coefficients (ADC) of each nutrient in the test diet and ingredients were calculated according to the following equations (Kleiber 1961, Forster 1999):

$$ADCN_{diet}=100-100\{\% \, Yt \text{ in diet} \times \% \text{ nutrient in feces}\}/\{\% \, Yt \text{ in feces} \times \% \text{ nutrient in diet}\}$$

$$ADCN_{ingredient}=\{(a+b)ADCN_t-(a)ADCN_r\}b^{-1}$$

where, $ADCN_{ingredient}$=apparent digestibility coefficient of the nutrient in the test ingredient Example 9

The following example illustrates the effect on growth and nutrient efficiency of fish fed meal made using a protein concentrate from barley.

A 12 week feeding study was conducted in which barley protein concentrate was substituted into both a fish meal based diet and a plant meal based diet (Table 4).

Semi-square polytanks (200-l) were supplied with 15° C. water at flow rate of 8-12 l min$^{-1}$ (flow to increase as fish grow). Photoperiod was held constant using metal halide lights on a timed system to provide 14 h light: 10 h dark. Each tank was be stocked with 3 fish averaging 15.5 g each and were fed the experimental diets to satiation.

TABLE 4

Composition of experimental diet for growth study with Barley Protein Concentrate

| Ingredient | BPC 1 F 100 | BPC 2 F 66 BP33 | BPC 3 F33 BP66 | BPC 4 BP 100 | BPC 5 SP 100 | BPC 6 SP66 BP33 | 7 SP33 BP66 |
|---|---|---|---|---|---|---|---|
| Fish meal | 34.25 | 22.84 | 11.42 | — | — | — | — |
| Soy PC | — | — | — | — | 25.43 | 16.95 | 8.48 |
| Barley Protein Conc. | — | 14.75 | 29.50 | 44.11 | — | 14.75 | 29.50 |
| Bio-soy. | — | — | — | — | — | — | — |
| Fish oil | 12.60 | 13.85 | 15.05 | 16.15 | 15.72 | 15.87 | 16.07 |
| Flour | 31.68 | 23.80 | 17.34 | 11.33 | 30.87 | 24.29 | 17.71 |
| Poultry by | 9.82 | 9.82 | 9.82 | 9.82 | 9.82 | 9.82 | 9.82 |
| Blood meal | 6.33 | 6.33 | 6.33 | 6.33 | 6.33 | 6.33 | 6.33 |
| Soybean meal | 3.42 | 3.42 | 3.42 | 3.42 | 3.42 | 3.42 | 3.42 |
| Lysine | — | 1.24 | 1.69 | 2.14 | 1.40 | 1.58 | 1.86 |
| Methionine | — | 0.40 | 0.60 | .59 | 0.59 | 0.59 | 0.69 |
| Threonine | — | 0.36 | 0.46 | .57 | 0.38 | 0.41 | 0.48 |
| Taurine | — | .50 | 0.50 | .50 | 0.50 | 0.50 | .50 |
| Vitamin premix | 1.00 | 1.00 | 1.00 | 1.00 | 1.00 | 1.00 | 1.00 |
| Choline Cl | 0.60 | 0.60 | 0.60 | 0.60 | 0.60 | 0.60 | .60 |
| Stay-C | 0.20 | 0.20 | 0.20 | 0.20 | 0.20 | 0.20 | .20 |
| Macro-premix | — | 0.30 | 0.60 | 0.89 | 0.89 | 0.89 | 0.89 |
| Di-calcium P | — | 0.49 | 1.37 | 2.25 | 2.65 | 2.51 | 2.34 |
| Trace min pre 3 | 0.10 | 0.10 | 0.10 | 0.10 | 0.10 | 0.10 | 0.10 |
| Protein, Crude | 42.33 | 43.92 | 43.85 | 43.16 | 42.47 | 42.96 | 43.37 |
| Protein, Digestible | 38.0 | 39.00 | 38.5 | 38.11 | 38.05 | 38.07 | 38.06 |
| Fat | 18.0 | 18.0 | 18.05 | 18.00 | 18.0 | 18.0 | 18.0 |
| Phosphorus | .98 | 0.90 | 0.91 | 0.91 | 0.90 | 0.91 | 0.90 |
| Met | .99 | 1.26 | 1.33 | 1.20 | 1.20 | 1.20 | 1.30 |
| Cys | .31 | 0.24 | 0.17 | 0.10 | 0.41 | 0.31 | 0.20 |
| Lys | 2.88 | 3.51 | 3.52 | 3.54 | 3.50 | 3.51 | 3.50 |
| Thr | 1.72 | 1.97 | 1.97 | 1.98 | 1.97 | 1.97 | 1.96 |

Experimental diets were randomly assigned to three tanks of fish for a total of 21 experimental units.

Tanks were cleaned daily and no fish mortality was observed. Fish were sampled at the beginning and end of trial for compositional analysis for the determination of protein and energy retention efficiencies.

Figure 3:
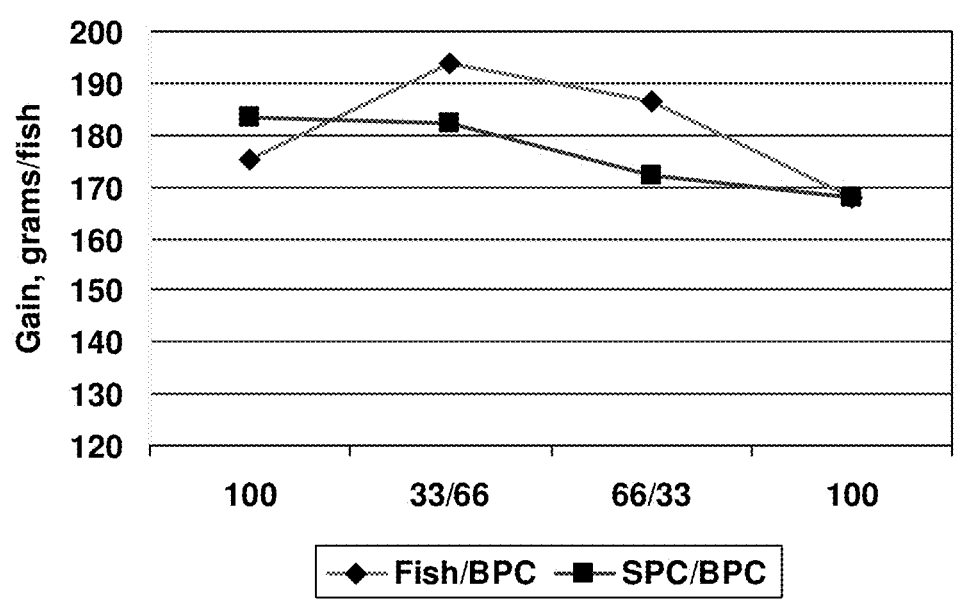
FIG. 3 Shows the effect of substituting fish meal or soy protein concentrate with barley protein concentrate.

FIG. 3 shows the effect of substituting fish meal or soy protein concentrate with barley protein concentrate. As can be seen in FIG. 3, feeding a diet with ⅓ and ⅔ replacement of fish meal with barley protein concentrate increased growth rate compared to feeding the 100% fish meal diet (means with different letters are different P<0.05). Feeding diets to trout with complete replacement of fish meal with barley protein concentrate resulted in equivalent growth.

We expect nutrient retention efficiency to be equivalent for fish fed any of the diets.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A protein concentrate made according to a process for producing a protein concentrate from a starch containing grain or oil seed, the process comprising:
   (i) grinding the starch containing grain to produce a ground starch containing grain;
   (ii) slurrying the ground starch containing grain with water to prepare a slurry comprising starch and glucans;
   (iii) solublizing starch and glucans comprising the slurry with enzymes to provide a solublized slurry;
   (iv) adding a fermentation organism to the solublized slurry;
   (v) fermenting the solublized slurry comprising the fermentation organism until fermentation is complete, thereby producing a fermented slurry;
   (vi) separating the fermented slurry into solid and liquid fractions;
   (vii) recovering the solid and liquid fractions;
   (viii) drying the recovered solid fraction at a temperature below that which would denature or damage proteins;
   thereby producing the protein concentrate according to a process for producing a protein concentrate from a starch containing grain or oil seed,
   wherein the protein concentrate comprises protein in an amount that is in a range that is between about 30% protein to about 70% protein on a dry basis.

2. An aquaculture feed comprising the protein concentrate of claim 1.

3. A method for producing a protein concentrate from a starch containing grain or oil seed having increased protein concentration, the method comprising:
   (i) grinding the starch containing grain to produce a ground starch containing grain;
   (ii) slurrying the ground starch containing grain with water to prepare a slurry comprising starch and glucans;
   (iii) solublizing starch and glucans comprising the slurry with enzymes to provide a solublized slurry;
   (iv) adding a fermentation organism to the solublized slurry;
   (v) fermenting the solublized slurry comprising the fermentation organism until fermentation is complete, thereby producing a fermented slurry;
   (vi) separating the fermented slurry into solid and liquid fractions;
   (vii) recovering the solid and liquid fractions;
   (viii) culturing an appropriate microbe to provide a cell mass in a culture medium comprising the liquid fraction recovered in step vii, and (ix) recovering the cell mass with the grain solids;
(x) drying the recovered solid fraction at a temperature below that which would denature or damage proteins;
thereby providing a protein concentrate having increased protein concentration relative to the protein concentration of a protein concentrate made by a method wherein steps viii and ix are omitted.

4. The method of claim 3, wherein the appropriate microbe is a member selected from the group consisting of *Rhizopus oryzae* and *Rhizopus microsporus*.

5. A protein concentrate made according to a process for producing a protein concentrate from a starch containing grain or oil seed, wherein the protein concentrate has an increased protein concentration, the process comprising:
   (i) grinding the starch containing grain to produce a ground starch containing grain;
   (ii) slurrying the ground starch containing grain with water to prepare a slurry comprising starch and glucans;
   (iii) solublizing starch and glucans comprising the slurry with enzymes to provide a solublized slurry;
   (iv) adding a fermentation organism to the solublized slurry;
   (v) fermenting the solublized slurry comprising the fermentation organism until fermentation is complete, thereby producing a fermented slurry;
   (vi) separating the fermented slurry into solid and liquid fractions;
   (vii) recovering the solid and liquid fractions then;
   (viii) culturing an appropriate microbe to provide a cell mass in a culture medium comprising the liquid fraction recovered in step vii, and
   (ix) recovering the cell mass together with the solids,
   (x) drying the recovered solid fraction at a temperature below that which would denature or damage proteins;
   thereby providing the protein concentrate having increased protein concentration relative to the protein concentration of a protein concentrate made by a method according to a process for producing a protein concentrate from a starch containing grain or oil seed wherein steps viii and ix are omitted.

6. The protein concentrate of claim 5, wherein the appropriate microbes is a member selected from the group consisting of *Rhizopus oryzae* and *Rhizopus microsporus*.

7. A method for producing a protein concentrate with an increased protein concentration from a starch containing grain, the method comprising:
   (i) grinding the starch containing grain to produce a ground starch containing grain;
   (ii) slurrying the ground starch containing grain with water;
   (iii) solublizing starch and glucans with enzymes;
   (iv) adding an appropriate microbe selected for cell mass production to the slurry;
   (v) fermenting the slurry comprising the appropriate microbe until fermentation is complete, thereby producing a slurry in which soluble sugars have been converted to cell mass;
   (vi) separating the slurry in which soluble sugars have been converted to cell mass into solid and liquid fractions;
   (vii) recovering the solid and liquid fractions;
   (viii) recovering the cell mass with the solid fraction, and drying the recovered solid fraction at a temperature below that which would denature or damage proteins;
   thereby producing a protein concentrate with increased protein concentration relative to the protein concentration of a protein concentrate made by an otherwise identical method wherein the appropriate microbe selected for cell mass production is not added.

8. The method of claim 7, wherein the appropriate microbe is a member selected from the group consisting of *Rhizopus oryzae* and *Rhizopus microsporus*.

9. A protein concentrate made according to a method for producing a protein concentrate with an increased protein concentration from a starch containing grain, the method comprising:
   (i) grinding the starch containing grain to produce a ground starch containing grain;
   (ii) slurrying the ground starch containing grain with water;
   (iii) solublizing starch and glucans with enzymes;
   (iv) adding an appropriate microbe selected for cell mass production to the slurry;
   (v) fermenting the slurry comprising the appropriate microbe until fermentation is complete, thereby producing a slurry in which soluble sugars have been converted to cell mass;
   (vi) separating the slurry in which soluble sugars have been converted to cell mass into solid and liquid fractions;
   (vii) recovering the solid and liquid fractions;
   (viii) recovering the cell mass with the solid fraction, and drying the recovered solid fraction at a temperature below that which would denature or damage proteins;
   thereby producing the protein concentrate with increased protein concentration relative to the protein concentration of a protein concentrate made by an otherwise identical method wherein the appropriate microbe selected for cell mass production is not added.

10. The protein concentrate of claim 9, wherein the appropriate microbes is a member selected from the group consisting of *Rhizopus oryzae* and *Rhizopus microsporus*.

* * * * *